United States Patent [19]

Röder et al.

[11] Patent Number: 4,550,079
[45] Date of Patent: Oct. 29, 1985

[54] DETERMINATION OF L(+)-TARTRATE OR D(+)-MALATE WITH L(+)-TARTRATE DEHYDROGENASE

[75] Inventors: Albert Röder, Seeshaupt; Hans Seidel, Tutzing; Friedrich Giffhorn, Göttingen, all of Fed. Rep. of Germany

[73] Assignee: Boehringer Mannheim GmbH, Mannheim, Fed. Rep. of Germany

[21] Appl. No.: 472,313

[22] Filed: Mar. 4, 1983

[30] Foreign Application Priority Data

Mar. 23, 1982 [DE] Fed. Rep. of Germany ....... 3210583

[51] Int. Cl.$^4$ .......................... C12Q 1/32; C12N 9/02; C12N 9/04
[52] U.S. Cl. ...................... 435/189; 435/26; 435/190
[58] Field of Search .......................... 435/189, 26, 190

[56] References Cited

PUBLICATIONS

Giffhorn, F., et al., Purification and Characterization of a Bifunctional L-(+)-Tartrate Dehydrogenase-D-(+-)-Malate Dehydrogenase (Decarboxylating) from *Rhodopseudomonas sphaeroides* Y, Journal of Bacteriology, vol. 155, No. 1, pp. 281-290, (1980).

*Primary Examiner*—Sidney Marantz
*Assistant Examiner*—Stephen C. Wieder
*Attorney, Agent, or Firm*—Felfe & Lynch

[57] ABSTRACT

A L(+)-tartrate dehydrogenase with L(+)-tartrate dehydrogenase and D(+)-malate dehydrogenase (decarboxylating) activity, which can be obtained from *Rhodopseudomonas sphaeroides*, and also a process for the production thereof.

Furthermore, a process and a reagent for the determination of L(+)-tartrate and of D(+)-malate.

12 Claims, 1 Drawing Figure

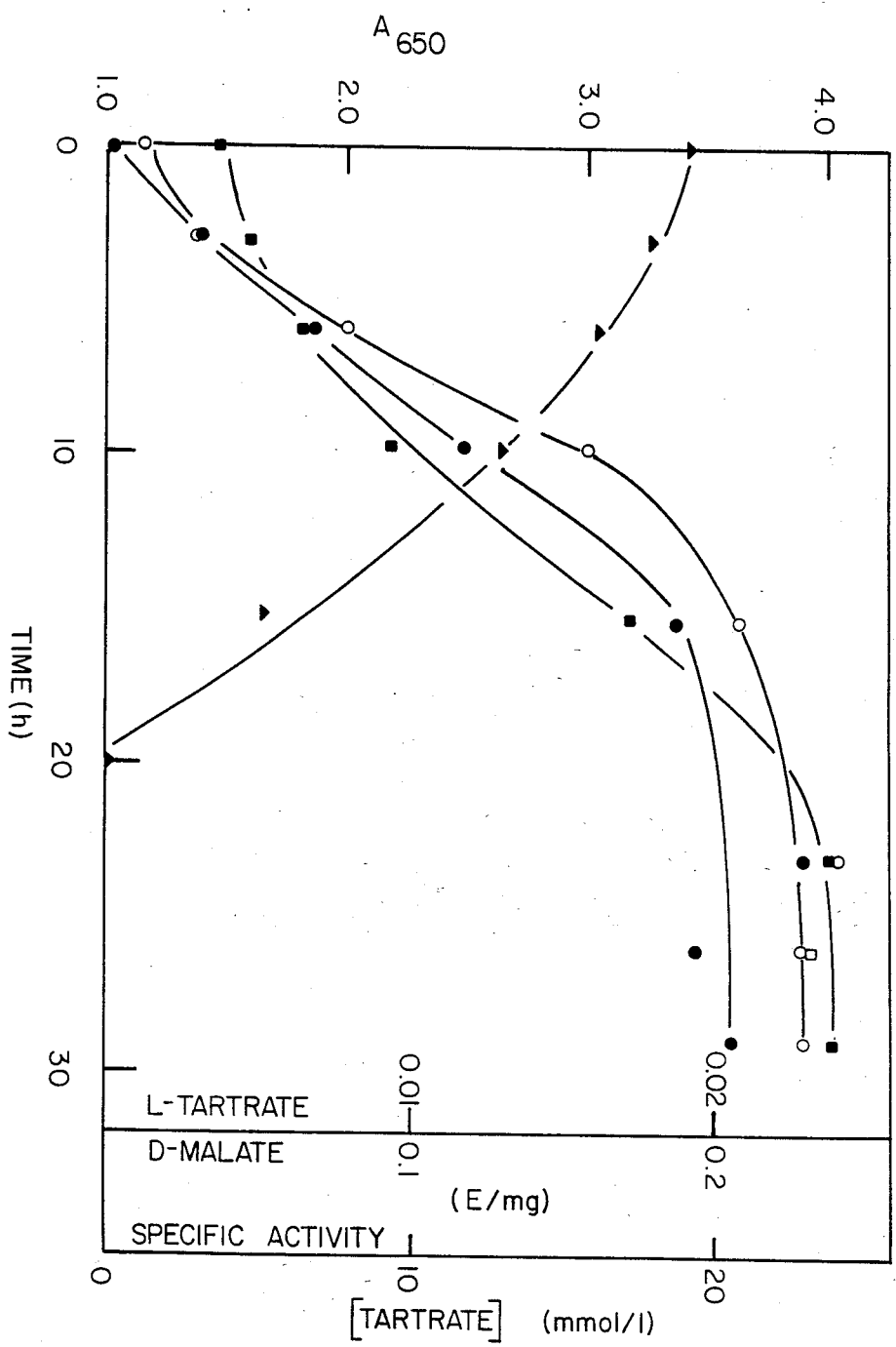

DETERMINATION OF L(+)-TARTRATE OR D(+)-MALATE WITH L(+)-TARTRATE DEHYDROGENASE

The present invention is concerned with a new L(+)-tartrate dehydrogenase and with a process for the preparation thereof, as well as with a process and a reagent for the determination of L(+)-tartrate and D(+)-malate.

Of the three possible stereoisomers of tartaric acid, L(+)-, D(−)- and meso-tartaric acid, L(+)-tartaric acid occurs widely in nature. The decomposition of tartaric acid by micro-organisms takes place by different reaction routes. One way of decomposition proceeds via an enzymatic oxidation with the help of tartrate dehydratase. This enzyme has been found, in particular, in Pseudomonas. However, because of its extraordinary instability, it still has not been possible to characterize it in detail and it has also not been possible to use it for a quantitative determination of tartaric acid or of tartrate ions.

Another route for the decomposition of tartaric acid is initiated by tartrate dehydrogenase. In the case of this reaction, the metastable product oxaloglycolic acid primarily results. Tartrate dehydrogenase activity has hitherto also been demonstrated in species of Pseudomonas. In principle, it is possible to carry out an enzymatic determination of tartaric acid on the basis of nicotinamide-adenine-dinucleotide (NAD) absorption not only with the help of tartrate dehydratase but also with tartrate dehydrogenase.

Various tartrate dehydrogenases are known (tartrate:NAD oxidoreductase, EC 1.1.1.93), for example from species of Pseudomonas and *Penicillium charlesii*. These enzymes catalyse the reaction of tartrate isomers in the presence of NAD as co-enzyme to give oxaloglycolate. Thus, for example, in J. Biol. Chem., 243, 2479–2485/1968, there is described a tartrate dehydrogenase from *Pseudomonas putida* which is able to react not only L(+)-tartrate but also mesotartrate in the presence of NAD, manganese (II) ions and monovalent cations to give oxaloglycolate. D(+)-Malate and L(−)-malate are not oxidised by this enzyme.

Because of the low specific activity and the great instability of the previously known enzyme preparations and of their unfavourable kinetic properties (high $K_m$ value for L(+)-tartrate), all attempts to use one of the enzymes for a routine quantitative determination of L(+)-tartaric acid have hitherto been unsuccessful. The hitherto known tartrate dehydrogenases were also not suitable for the detection of L(+)-tartrate because, in addition to its L-form, they also break down the meso-form, which also occurs in nature.

Therefore, it is an object of the present invention to provide a new L(+)-tartrate dehydrogenase which is sufficiently stable, displays favourable kinetic properties and, of the possible tartrate isomers, quite specifically reacts the L(+)-tartrate isomer.

Surprisingly, we have now found that from species of Rhodopseudomonas and especially from strains of *Rhodopseudomonas sphaeroides* which have been cultured phototrophically (light, anaerobically) or heterotrophically (darkness, aerobically) on L(+)-tartrate there can be isolated an L(+)-tartrate dehydrogenase which is sufficiently stable, displays a sufficiently specific activity towards L(+)-tartrate, possesses good kinetic properties and is, therefore, suitable for the detection of L(+)-tartrate.

The L(+)-tartrate dehydrogenase isolated from strains of *Rhodopseudomonas sphaeroides* also catalyses the reaction of D(+)-malate to pyruvate and carbon dioxide, i.e. besides the L(+)-tartrate dehydrogenase activity, it also displays a D(+)-malate dehydrogenase (decarboxylating) activity. Thus, the new enzyme can also be used for the detection of D(+)-malate.

Thus, the present invention provides a new L(+)-tartrate dehydrogenase which not only displays an L(+)-tartrate dehydrogenase activity but also a D(+)-malate dehydrogenase (decarboxylating) activity. Not only in the case of the oxidation of L(+)-tartrate but also in the case of the oxidation of D(+)-malate, the new enzyme according to the present invention requires NAD as specific co-substrate. Furthermore, the presence of $Mn^{2+}$ or $Mg^{2+}$ ions is necessary. The optimum pH value for both activities is 7.5 to 9.0. The molecular weight of the new enzyme is about 160,000. The enzyme consists of four subunits, each with a molecular weight of 38,500. The isoelectric point is at pH 5.0 to 5.2. The temperature optimum is 50° C. and the activating energies ($\Delta H°$) are 54.4 kJ/mol for D(+)-malate and 71.5 kJ/mol for L(+)-tartrate.

The present invention also provides a process for the preparation of the new L(+)-tartrate dehydrogenase. Various strains of *Rhodopseudomonas sphaeroides* can be used for the production of the L(+)-tartrate dehydrogenase according to the present invention. The strains *Rhodopseudomonas sphaeroides* DSM 158, DSM 159, DSM 160 and DSM 2303, which have been deposited at the German Collection for Microorganisms (DSM), are especially suitable.

The culturing of the *Rhodopseudomonas sphaeroides* strain can be carried out phototrophically or heterotrophically in the usual manner. The growth behaviour of the micro-organisms displays only a low dependence upon the fundamental culture conditions.

The nutrient medium used is one which contains L(+)-tartaric acid as an essential component. Furthermore, such a medium also contains conventional substances, for example various inorganic salts, trace elements and vitamins. Both activities of the L(+)-tartrate dehydrogenase (towards L(+)-tartrate and D(+)-malate) are induced in parallel by L(+)-tartrate. After the decomposition of the inductor, the growth of the culture and the enzyme formation cease (see FIG. 1 of the accompanying drawing). The activity of the L(+)-tartrate dehydrogenase is also maintained during the course of a comparatively long stationary phase so that proteolytic processes can be excluded.

The best growth conditions are achieved when the culture medium contains L(+)-tartrate in an initial concentration of 20 to 50 and preferably of 40 to 50 mmol/liter.

The rate of growth can be further increased by the addition of various substances, for example polyhydroxy alcohols and carbohydrates, to the nutrient medium. Thus, for example, an addition of glycerol or glucose in a concentration of, in each case, 5 to 20 and preferably 10 mmol/liter, brings about an increase of the activity of the L(+)-tartrate dehydrogenase.

After the conclusion of the culturing, the cells are harvested in known manner. In addition to the L(+)-tartrate dehydrogenase activity, the cell extracts always display a D(+)-malate dehydrogenase (decarboxylating) activity, as well as an L(−)-malate dehydrogenase and aldehyde dehydrogenase activity. The crude cell extracts can be further purified by known methods, for example protamine sulphate precipitation, heating step, ammonium sulphate precipitation, chromtographic purification and the like.

In the case of all purification steps, the ratio of D(+)-malate dehydrogenase (decarboxylating) activity to the L(+)-tartrate dehydrogenase activity remains constant, whereas the L(−)-malate dehydrogenase and aldehyde dehydrogenase activity can be quantitatively removed. This is an indication that the D(+)-malate dehydrogenase (decarboxylating) activity is a component of the L(+)-tartrate dehydrogenase. The following experiments and conclusions support this:

1. The specific activities of cells which have been grown on L(+)-tartrate were compared with the specific activity of cells which have been grown on acetate, succinate, fumarate or L(−)-malate and also on D(+)-malate. It has been shown that not only the L(+)-tartrate dehydrogenase activity but also the D(+)-malate dehydrogenase (decarboxylating) activity of cells grown on L(+)-tartrate is 40 to 50 times higher than in extracts of cells which have been grown on acetate, succinate, fumarate or L(−)-malate and 5 times higher than in extracts of cells which have been grown on D(+)-malate. It follows from this that L(+)-tartrate induces both activities in the same way and, in comparison with D(+)-malate, it is the better inducer.

2. Both activities have the same pH optimum. They both require the same effectors and co-substrates.

3. Gel filtration on Sepharose 6B leads to the elution of both activities within a symmetrical peak.

4. Both activities are inactivated at 45°, 50° and 55° C. at the same rate.

5. By means of activity staining with phenazine methosulphate and p-nitro blue tetrazolium chloride in polyacrylamide gels, the same bands could be detected as being L(+)-tartrate active as well as D(+)-malate active.

In the following Table 1, for the L(+)-tartrate dehydrogenase (TDH) according to the present invention from various strains of *Rhodopseudomonas sphaeroides*, there are given the specific activities of the TDH (U/mg) towards L(+)-tartrate in the crude extract and after the heating step:

TABLE 1

| strain | specific activity (U/mg) towards L(+)-tartrate | |
|---|---|---|
| | in the crude extract | after the heating step |
| DSM 158 | 0.006 | 0.014 |
| DSM 159 | 0.01 | 0.022 |
| DSM 160 | 0.017 | 0.028 |
| DSM 2303 | 0.02 | 0.032 |

The L(+)-tartrate dehydrogenase (TDH) according to the present invention is able to catalyse the following two enzymatic reactions with a good reactivity and selectivity:

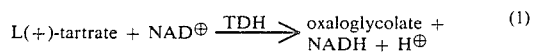 (1)

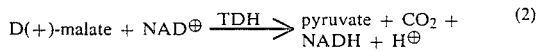 (2)

In the case of both enzymatic reactions, the pH optimum is at 7.5 to 9.0. For both reactions, nicotinamide-adenine-dinucleotide (NAD) is needed as co-substrate and $Mn^{2+}$ or $Mg^{2+}$ ions as essential cations. The following $K_m$ values were measured in known manner (30° C.; 0.1 mol/liter tris-HCl buffer, pH 8.5; 0.4 mmol/liter $MnCl_2$; 1 mmol/liter mercaptoethanol; 50 mmol/liter ammonium sulphate; 20 mmol/liter KCl; 0.12 U L(+)-tartrate dehydrogenase; the $K_m$ values for $NAD^+$ or $Mn^{2+}$ were, in each case, determined at the saturation concentration of the other reaction components):

TABLE 2

| L(+)-tartrate | $2.3 \times 10^{-3}$ mol/liter |
| $NAD^+$ | $2.8 \times 10^{-4}$ mol/liter |
| $Mn^{2+}$ | $1.6 \times 10^{-5}$ mol/liter |
| D(+)-malate | $1.7 \times 10^{-4}$ mol/liter |
| $NAD^+$ | $1.3 \times 10^{-4}$ mol/liter |
| $Mn^{2+}$ | $1.6 \times 10^{-5}$ mol/liter |

The L(+)-tartrate dehydrogenase according to the present invention is substantially stable. In lyophilized form or in solution, the enzyme only slightly loses its activity at 25° C. within the course of 30 days. The L(+)-tartrate dehydrogenase is preferably used in the form of a solution in an ammonium sulphate solution (100 mmol/liter). Thus, a special addition of ammonium ions to the test compositions described in the following is unnecessary.

The stability of the L(+)-tartrate dehydrogenase, its high specificity and its high affinity for L(+)-tartrate makes the enzyme according to the present invention suitable for the determination of L(+)-tartrate according to the above-given reaction 1).

Therefore, the present invention also provides a process and a reagent for the determination of L(+)-tartrate in liquids, wherein L(+)-tartrate is converted, in the presence of NAD and $Mn^{2+}$ or $Mg^{2+}$ ions, with the help of L(+)-tartrate dehydrogenase, into oxaloglycolate, with the formation of NADH and the resultant NADH is determined in known manner.

The determination of the resulting NADH can, for example, take place photometrically by measuring the increase of the extinction at 365 nm (Hg). For this purpose, the tartrate-containing sample solution is preferably mixed with a buffer system of pH 7.5 to 9.0, for example with a tris-HCl buffer of pH 8.5. NAD and $Mn^{2+}$ or $Mg^{2+}$ ions, as well as possibly further adjuvants, such as detergents and/or stabilising agents, are added thereto. The enzymatic reaction is initiated with the L(+)-tartrate dehydrogenase according to the present invention. The measurement is advantageously carried out at ambient temperature or at a slightly elevated temperature.

At ambient temperature, the period of the reaction is from 25 to 60 minutes. In the case of the use of 0.1 to 3.0 U tartrate dehydrogenase per test, 3 to 50% of tartrate is thereby detected. If the reaction temperature is increased to 30° to 40° C., then, in the case of 3 U tartrate dehydrogenase per test, there is achieved a 50% tartrate reaction within the course of 20 minutes.

The substances necessary for the detection reaction are preferably used in the following concentrations:
0.01 to 1.00 mol/liter buffer, pH 7.5 to 9.0
0.1 to 15 mmol/liter manganese (II) or magnesium salt
2 to 50 mmol/liter NAD
0.01 to 5 U/ml. of L(+)-tartrate dehydrogenase according to the present invention in aqueous ammonium sulphate solution (100 mmol/liter).

The following test composition is especially preferred:

20 to 50 mmol/liter tris-HCl buffer, pH 8.5
4 to 10 mmol/liter manganese (II) chloride
15 to 25 mmol/liter NAD
0.1 to 2 U/ml. of L(+)-tartrate dehydrogenase according to the present invention in aqueous ammonium sulphate solution (100 mmol/liter).

A tartrate reaction is to be achieved more advantageously and more quickly when reaction (1) is coupled with the following reaction (3):

$$NADH + \text{tetrazolium salt} + H^{\oplus} \rightarrow NAD^{\oplus} + \text{formazan} \quad (3)$$

For this purpose, a tetrazolium salt, an appropriate catalyst as well as possibly further adjuvants are additionally added to the test solution. For example, the test reaction can be carried out with nitrotetrazolium blue (NTB) as tetrazolium salt in the presence of potassium chloride and ammonium chloride.

The reaction takes place in about 30 minutes, about 25 to 30% of the tartrate thereby being detected. When using 2,5-diphenyl-3-[4,5-dimethylthiazolyl-(2)]-tetrazolium bromide (MTT) as the tetrazolium salt, the reaction velocity is markedly increased, 50% of the tartrate being reacted within a period of about 10 minutes.

An advantageous embodiment of the L(+)-tartrate determination according to the present invention is the coupling of the enzymatic tartrate decomposition (1) with a tetrazolium salt reaction (3), using 2-p-iodophenyl-3-p-nitrophenyl-5-phenyltetrazolium chloride (INT) as the tetrazolium salt and also diaphorase and polyoxyethylene alkyl aryl ether (Triton X 100). This determination variant is advantageously carried out with the following test concentrations:
0.01 to 1.00 mol/liter buffer, pH 7.5–9.0
1 to 100 mmol/liter alkali metal chloride
0.1 to 100 mmol/liter manganese (II) or magnesium salt
1 to 100 mMol/liter NAD
0.05 to 1.0% (v/v) polyoxyethylene alkyl aryl ether (Triton X 100)
0.1 to 5.0 U/ml. diaphorase
0.01 to 1.0 mmol/liter tetrazolium salt
0.01 to 10 U/ml. L(+)-tartrate dehydrogenase according to the present invention in aqueous ammonium sulphate solution (100 mmol/liter).

The following test composition is especially preferred:
65 to 80 mmol/liter tris-HCl buffer, pH 8.5
10 to 20 mmol/liter potassium chloride
0.3 to 0.6 mmol/liter manganese (II) chloride
4 to 10 mmol/liter NAD
0.1 to 0.2% (v/v) polyoxyethylene alkyl aryl ether (Triton X 100)
0.5 to 1.0 U/ml. diaphorase
0.05 to 0.2 mmol/liter INT
0.15 to 0.25 U/ml. L(+)-tartrate dehydrogenase according to the present invention in aqueous ammonium sulphate solution (100 mmol/liter).

The L(+)-tartrate dehydrogenase according to the present invention also oxidises D(+)-malate in the presence of NAD and manganese (II) ions to pyruvate and carbon dioxide. The NADH thereby formed can also be determined by known methods, for example directly photometrically at 365 nm (Hg) or also after the addition of a tetrazolium salt and possibly of further adjuvants via the formazan dyestuff being formed.

Thus, the present invention also provides a process and a reagent for the determination of D(+)-malate in solutions, especially in fruit juices, which is characterised in that D(+)-malate is oxidised in the presence of NAD and $Mn^{2+}$ or $Mg^{2+}$ ions to give pyruvate and carbon dioxide, with the formation of NADH, and the resultant NADH is measured by known methods.

The determination process is carried out at a constant temperature in the range of from 20° to 40° C. and preferably of from 25° to 30° C. For the determination of D(+)-malate, a D(+)-malate-containing sample is brought into contact with a solution which, in a buffer system with a buffering range of from pH 7.5 to 9.0 and preferably in tris buffer of pH 8.5, contains NAD and manganese (II) chloride, as well as possibly further additives, for example detergents and/or stabilising agents. The enzymatic reaction is started by the addition of the L(+)-tartrate dehydrogenase. From the extinctions before the addition of the enzyme and after ending of the enzymatic reaction, there is determined the extinction difference from which the initial concentration of D(+)-malate in the sample can be determined. In order to be able to take into account the absorption of the reagents used, a blank measurement is carried out parallel to the sample, in which the sample is replaced by a corresponding amount of water.

The substances necessary for the determination are advantageously used in the following concentrations:
0.01 to 1 mol/liter buffer, pH 7.5 to 9.0
0.1 to 100 mmol/liter manganese (II) or magnesium salt
1 to 100 mmol/liter NAD
0.01 to 1 U/ml. L(+)-tartrate dehydrogenase according to the present invention in aqueous ammonium sulphate solution (100 mmol/liter).

The following test composition is especially preferred:
0.05 to 0.2 mmol/liter tris-HCl buffer, pH 8.5
3 to 10 mmol/liter manganese (II) chloride
5 to 20 mmol/liter NAD
0.01 to 0.1 U/ml. L(+)-tartrate dehydrogenase according to the present invention in aqueous ammonium sulphate solution (100 mmol/liter).

The concentration of D(+)-malate in the test solution should not exceed a value of 0.25 mmol/liter. If higher concentrations of D(+)-malate are to be expected in the sample to be tested, then the advantageous concentration range of below 0.25 mmol/liter can be obtained by appropriate dilution.

The detection of D(+)-malate with the L(+)-tartrate dehydrogenase according to the present invention is very specific. L(−)-Malic acid and L(−)-malate do not react.

The determination of D(+)-malate in fruit juices is of particular importance because D(+)-malic acid is often added to fruit juices in an inadmissible manner. Usually, fruit juices do not contain any D(+)-malic acid. Consequently, a positive detection reaction with L(+)-tartrate dehydrogenase indicates a falsification of the fruit juice by the addition of D(+)-malic acid.

In contradistinction to the above-described decomposition of tartrate with the help of the L(+)-tartrate dehydrogenase, which is only achieved up to 30 to 50%, the decomposition of D(+)-malate with the help of the L(+)-tartrate dehydrogenase is complete. D(+)-Malic acid added to a solution is detected quantitatively.

The following Examples are given for the purpose of illustrating the present invention:

EXAMPLE 1

L(+)-Tartrate dehydrogenase from *Rhodopseudomonas sphaeroides* DSM 160

Growth of the cells

Cells of *Rhodopseudomonas sphaeroides* DSM 160 are grown anaerobically in light for 36 hours on a culture medium which contains the following components:

3.0 g. L(+)-tartaric acid
1.0 g. monopotassium dihydrogen phosphate
0.4 g. magnesium sulphate heptahydrate
0.4 g. sodium chloride
0.5 g. ammonium chloride
0.05 g. calcium chloride dihydrate
10 ml. trace element solution SL 4 according to N. Pfennig et al. (Arch. Mikrobiol., 55, 245–256/1966)
ad 1 liter water
pH 6.7 adjusted with a mixture of 5M each of potassium hydroxide and sodium hydroxide.

Culturing in aerobic shake culture 300 ml. amounts of the cell suspension obtained in the above manner are incubated in 1 liter Erlenmeyer long-necked flasks with baffle plates at 30° C. on a shaking bench at 150 r.p.m., with the addition of the above-mentioned culture medium.

In FIG. 1 of the accompanying drawing there is plotted the course of the tartrate decomposition (-▲-▲-), of the absorption at 650 nm (-■-■-) and of the specific activity of the TDH towards L(+)-tartrate (-◐-◐-) and D(+)-malate (-o-o-).

Culturing in a fermenter

The culturing experiments in shaken flasks can readily be transferred to fermenter batches. 10 Liter fermenters (Braun Biostat) are filled with a culture medium which contains 10.5 g./liter L(+)-tartaric acid (70 mmol/liter) and 8 g./liter yeast extract. During the culturing, aeration with air is carried out at a rate of 5 liters/minute. The temperature is maintained at 30° C. The speed of stirring is 400 r.p.m. During the period of culturing, the pH value is kept constant at pH 6.7 by the addition of appropriate amounts of hydrochloric acid or phosphoric acid.

Fermenter I is inoculated with 10% of an aerobic preculture, the pH value being kept constant with 1N hydrochloric acid. Fermenter II is inoculated with 10% of an aerobic preculture, the pH value being kept constant with 5M phosphoric acid (consumption about 140 ml.). Fermenter III is inoculated with 20% of residue from Fermenter II, the pH value being kept constant with 5M phosphoric acid as in the case of Fermenter II. After 12 hours, complete culture medium was introduced.

As in the case of culturing in shaken flasks, the mentioned parameters are determined after 24 hours. Under the justifiable assumption that $A_{650}=1$ corresponds to about 6 U TDH/liter, in the case of the individual fermenter batches, the following enzyme yields are obtained:

| fermenter | TDH |
| --- | --- |
| I | 42 |
| II | 54 |
| III | 90 |

Enrichment of the L(+)-tartrate dehydrogenase

The cell mass obtained by the culturing is suspended in a buffer solution (3 ml. buffer/g. of cell mass), which contains 100 mmol/liter tris-HCl buffer (pH 7.0), 0.4 mmol/liter manganese (II) chloride and 5 mmol/liter mercaptoethanol. The cells are disentegrated with a French press at a pressure of from 980 to 1400 kg./cm². Cell debris is subsequently separated off by centrifuging (30 minutes at 20,000 g).

Protamine sulphate solution is added dropwise to the cell extract obtained. The precipitate obtained is centrifuged off in the manner described above.

The supernatant is heated to 53° C. for 10 minutes. The protein solution is subsequently cooled in ice and centrifuged as described above.

The enzyme is precipitated out from the supernatant obtained by adding a saturated ammonium sulphate solution which has been mixed with 5 mmol/liter mercaptoethanol.

The precipitate is suspended in a dialysis buffer which contains 50 mmol/liter tris-HCl buffer (pH 7.0), 0.4 mmol/liter manganese (II) chloride and 5 mmol/liter mercaptoethanol. It is dialyzed for 12 to 15 hours against a 50 fold volume of dialysis buffer. A residual turbidity is centrifuged off.

A further purification can take place by chromatography on DEAE-cellulose and/or on a DEAE-Sephadex A50 ion exchanger.

The following Table 3 summarises the protein yields, the activities towards (L+)-tartrate, D(+)-malate and L(−)-malate, as well as the specific activity towards (L+)-tartrate after the various purification operations:

TABLE 3

| enrichment step | total protein (mg.) | total activity (U) | | | spec. activity (U/mg) L(+)-tart-rate-DH | factor |
| --- | --- | --- | --- | --- | --- | --- |
| | | L(+)-tart-rate | D(+)-mal-ate | L(−)-mal-ate | | |
| crude extract | 1234 | 20.8 | 228 | 2004 | 0.017 | 1 |
| protamine sulphate precip. | 1134 | 15.2 | 209 | 1980 | | |
| heating step | 362 | 19.5 | 218 | 27 | 0.054 | 3.2 |
| ammonium sulphate precip. | 199 | 19.0 | 215 | 11 | 0.095 | 5.6 |
| DEAE-cellulose | 50 | 14.0 | 161 | — | 0.28 | 16 |
| DEAE-Sephadex A50 | 11 | 13.5 | 155 | — | 1.23 | 72 |

The specificity of the L(+)-tartrate dehydrogenase is determined in known manner with the enriched enzyme. For this purpose, to the enzyme-containing solution there is added, for example, tris-HCl buffer (pH 8.5) and an NAD solution containing ammonium, potassium and manganese (II) ions. The reaction is started by the addition of the substrates given in the following Table in a concentration of 10 μmol/ml. The test batches each contain 20 μl. of enzyme with the exception of the case of D(+)-malate in which only 2 μl. of enzyme is added.

The measurement results are given in the following Table 4:

TABLE 4

| substrate | ΔE/minute |
| --- | --- |
| L(+)-tartrate | 0.47 |
| D(−)-tartrate | 0 |
| meso-tartrate | 0 |
| L(−)-malate | 0 |
| D(+)-malate | 0.43 |
| lactate | 0 |
| hydroxypyruvate | 0 |
| glycolate | 0 |
| glycerate | 0 |
| succinate | 0 |
| isocitrate | 0 |
| citrate | 0 |
| NADP$^+$ + L(+)-tartrate | 0 |
| NADP$^+$ + D(+)-malate | 0 |

EXAMPLE 2

L(+)-Tartrate dehydrogenase from *Rhodopseudomonas sphaeroides* DSM 2303

*Rhodopseudomonas sphaeroides* DMS 2303 is precultured as described in Example 1, cultured in a fermenter and harvested in the usual way. Thereafter, the crude L(+)-tartrate dehydrogenase is subjected to known purification operations, such as a heating step, ammonium sulphate fractionation, chromatographic separation over DEAE-cellulose and DEAE-Sephadex A50. An enzyme is obtained with a specific activity towards L(+)-tartrate of 400 U/g. of protein.

Foreign activities still present in the crude extract, such as L(−)-malate dehydrogenase and aldehyde dehydrogenase activity, can be removed in the course of purifying the enzyme. The following Table 5 shows the decrease of these foreign activities after the individual purification steps:

TABLE 5

| purification step | total activity (U) | |
| --- | --- | --- |
| | L(−)-malate dehydrogenase | aldehyde dehydrogenase |
| cell extract | 1270 | |
| ammonium sulphate precipitation | 780 | 9.3 |
| DEAE-cellulose | 63 | 1.2 |
| DEAE-Sephadex A50 | 0 | 0 |

EXAMPLE 3

Photometric determination of L(+)-tartrate

The following solutions are pipetted into synthetic resin cuvettes (layer thickness: 1 cm.; test volume: 1.32 ml.):

| | blank (ml.) | sample (ml.) | concentration in the test |
| --- | --- | --- | --- |
| tris, pH 8.5, 50 mmol/l. | 1.00 | 1.00 | 38 mmol/l. |
| manganese chloride, 70 mmol/l. | 0.10 | 0.10 | 5.3 mmol/l. |
| NAD, 230 mmol/l. | 0.10 | 0.10 | 17.1 mmol/l. |
| sample solution (tartaric acid) | — | 0.10 | up to about 250 μmol/l. |
| water | 0.10 | — | |

The contents of the sample cuvette as well as of the blank cuvette are mixed. Thereafter, the initial extinction $E_1$ is measured at the wavelength of 365 nm (Hg) (measurement temperature 37° C. or ambient temperature; measurement against air). For the commencement of the enzymatic reaction, both cuvettes are mixed with 0.1 to 3.0 U ($\doteq$0.03 to 1 U/ml. of test solution) of the L(+)-tartrate dehydrogenase according to the present invention. The contents are again mixed up and incubated at 37° C. or at ambient temperature until the reaction comes to a stop. Thereafter, the extinction value $E_2$ is measured. From the extinction differences $\Delta E = E_2 - E_1$ there is determined the initial tartrate concentration in the sample solution with the help of the equation:

$$C = \Delta E \times 0.5827 \ [g./l.]$$

EXAMPLE 4

Tartrate determination via formazan formation

Semi-micro cuvettes (layer thickness: 1 cm.; test volume 1.475 ml.) are filled with the following solutions:

| | blank (ml.) | sample (ml.) | concentration in the test |
| --- | --- | --- | --- |
| tris, pH 8.5, 100 mmol/l. | 1.000 | 1.000 | 68 mmol/l. |
| KCl, 220 mmol/l. | 0.100 | 0.100 | 15 mmol/l. |
| MnCl$_2$, 120 mmol/l. | 0.005 | 0.005 | 0.41 mmol/l. |
| NAD, 75 mmol/l. | 0.100 | 0.100 | 5.1 mmol/l. |
| Triton X 100, 10% | 0.020 | 0.020 | 0.13% |
| diaphorase, 16 U/ml. | 0.050 | 0.050 | 0.54 U/ml. |
| INT, 1.19 mmol/l. | 0.100 | 0.100 | 0.08 mmol/l. |
| sample (tartaric acid) | — | 0.100 | up to 40 μmol/l. |
| water | 0.100 | — | |

The contents of the sample cuvette, as well as of the blank cuvette, are mixed. The initial extinction $E_1$ is measured at a wavelength of 492 nm (Hg) measurement temperature 37° C.; measurement against air). For starting the enzymatic reaction, both cuvettes are mixed with 0.01 ml. of an L(+)-tartrate dehydrogenase preparation according to the present invention, which has an activity of 46 U/ml. (end concentration in the test batch 0.36 U/ml.). The contents of the cuvettes are again mixed up and incubated at 37° C. until the reaction comes to a stop. Thereafter, the extinction $E_2$ is measured.

The enzymatic reaction is completely finished after about 20 minutes. The extinction difference $\Delta E$ is about 0.8. From the extinction difference $\Delta E$ for a sample with an unknown tartrate content, the initial tartrate concentration can be determined by comparison with standard values determined by the measurement of known tartrate concentrations.

EXAMPLE 5

Determination of D(+)-malate in fruit juices

Cuvettes (layer thickness: 1 cm.; test volume: 2.96 ml.; measurement wavelength: 365 nm (Hg)) are filled at 25° C. with the following solutions:

| starting solution | sample (ml.) | blank (ml.) | concentration in the test |
| --- | --- | --- | --- |
| tris buffer, pH 8.5; 0.1 mol/l. | 2.70 | 2.70 | 0.09 mol/l. |
| manganese chloride, 0.19 mol/l. | 0.01 | 0.01 | 0.6 mmol/l. |
| NAD, 0.15 mol/l. | 0.10 | 0.10 | 5.1 mmol/l. |

-continued

| starting solution | sample (ml.) | blank (ml.) | concentration in the test |
|---|---|---|---|
| sample solution (about 1 mg. D-malic acid/ml.) | 0.10 | — | up to 0.25 mmol/l. |
| water | — | 0.10 | |

The contents of both cuvettes are mixed and the extinction $E_1$ measured after about 2 minutes. Thereafter, the enzymatic reaction is started by the addition of 0.05 ml. of the tartrate dehydrogenase according to the present invention with an activity of 1.8 U/ml. (concentration in the test volume 30 mU/ml.). After the extinction no longer increases noticeably (after 5 to 10 minutes), the extinction $E_2$ is measured for the sample and blank. From the extinction differences $E_2-E_1$ for the sample and blank there is calculated the value $\Delta E$ and the content of D(+)-malic acid or of D(+)-malate is calculated from the formula:

$$D(+)\text{-malic acid} = \Delta E \times 1.167 \text{ [g./l. sample solution]}$$

According to the above-described test conditions, the D-malic acid is detected up to 99%.

It will be understood that the specification and examples are illustrative but not limitative of the present invention and that other embodiments within the spirit and scope of the invention will suggest themselves to those skilled in the art.

What is claimed is:

1. Process for the determination of L(+)-tartrate in solution, comprising
    (a) adding to said solution NAD and $Mn^{2+}$ ions, and L(+)-tartrate dehydrogenase, said L(+)-tartrate dehydrogenase having L(+)-tartrate dehydrogenase and D(+)-malate dehydrogenase activities;
    (b) measuring the NADH resulting from step (a); and
    (c) relating the measurement of step (b) to the amount of L(+)-tartrate originally present in the solution.

2. The process of claim 1 wherein the NADH is determined photometrically.

3. The process according to claim 1 wherein the NADH is reacted with a tetrazolium salt and catalyst to form formazan which is then determined photometrically.

4. The process according to claim 3 wherein the tetrazolium salt is 2-p-iodophenyl-3-p-nitrophenyl-5-phenyltetrazolium chloride, the catalyst is diaphorase and an adjuvant is added, said adjuvant being polyoxyethylene alkyl aryl ether (Triton X 100).

5. Reagent for the determination of L(+)-tartrate according to claim 3 which contains
    0.01 to 1.00 mol/l. buffer, pH 7.5–9.0,
    1 to 100 mmol/l. alkali metal chloride,
    0.1 to 100 mmol/l. manganese (II) or magnesium salt,
    1 to 100 mmol/l. NAD,
    0.05 to 1.0% (v/v) polyoxyethylene alkyl aryl ether (Triton X 100),
    0.1 to 5 U/ml. diaphorase,
    0.01 to 1.0 mmol/l. tetrazolium salt, and
    0.01 to 10 U/ml. L(+)-tartrate dehydrogenase having L(+)-tartrate dehydrogenase and D(+)-malate dehydrogenase (decarboxylating) activity.

6. Reagent for the determination of L(+)-tartrate according to claim 5 which contains
    65 to 80 mmol/l. tris-HCl buffer, pH 8.4,
    10 to 20 mmol/l. potassium chloride,
    0.3 to 0.6 mmol/l. manganese (II) chloride,
    4 to 10 mmol/l. NAD,
    0.1 to 0.2% (v/v) polyoxyethylene alkyl aryl ether (Triton X 100),
    0.5 to 1.0 U/ml. diaphorase,
    0.05 to 0.2 mmol/l. 2-p-iodophenyl-3-p-nitrophenyl-5-phenyltetrazolium chloride (INT), and
    0.15 to 0.25 U/ml L(+)-tartrate dehydrogenase having L(+)-tartrate dehydrogenase and D(+)-malate dehydrogenase (decarboxylating) activity.

7. A reagent for the determination of L(+)-tartrate according to claim 7 which contains
    0.01 to 1.00 mol/l. buffer, pH 7.5–9.0,
    0.1 to 15 mmol/l. manganese (II) or magnesium salt,
    2 to 50 mmol/l. NAD, and
    0.01 to 5 U/ml. L(+)-tartrate dehydrogenase having L(+)-tartrate dehydrogenase and D(+)-malate dehydrogenase (decarboxylating) activity.

8. Reagent according to claim 5 which contains
    20 to 50 mmol/l. tris buffer, pH 8.5,
    4 to 10 mmol/l. manganese (II) chloride,
    15 to 25 mmol/l. NAD, and
    0.1 to 2 U/ml. L(+)-tartrate dehydrogenase having L(+)-tartrate dehydrogenase and D(+)-malate dehydrogenase (decarboxylating) activity.

9. A process for the determination of D(+)-malate in solution, comprising
    (a) adding to said solution NADH and $Mn^{2+}$ ions, and L(+)-tartrate dehydrogenase, said L(+)-tartrate dehydrogenase having L(+)-tartrate dehydrogenase and D(+)-malate dehydrogenase (decarboxylating) activities,
    (b) measuring the NADH resulting from step (a); and
    (c) relating the measurement of step (b) to the amount of D(+)-malate originally present in the solution.

10. The process of claim 9 wherein the NADH is determined photometrically.

11. Reagent for the determination of D(+)-malate according to claim 9 which contains
    0.01 to 1 mol/l. buffer, pH 7.5 to 9.0
    0.1 to 100 mmol/l. manganese (II) or magnesium salt,
    1 to 100 mmol/l. NAD, and
    0.01 to 1 U/ml. L(+)-tartrate dehydrogenase having L(+)-tartrate dehydrogenase and D(+)-malate dehydrogenase (decarboxylating) activity.

12. Reagent according to claim 11 which contains
    0.05 to 0.2 mmol/l. tris-HCl buffer, pH 8.5,
    3 to 10 mmol/l. manganese (II) chloride,
    5 to 20 mmol/l. NAD, and
    0.01 to 0.1 U/ml. L(+)-tartrate dehydrogenase having L(+)-tartrate dehydrogenase and D(+)-malate dehydrogenase (decarboxylating) activity.

* * * * *

UNITED STATES PATENT AND TRADEMARK OFFICE
CERTIFICATE OF CORRECTION

PATENT NO. : 4,550,079
DATED : October 29, 1985
INVENTOR(S) : Albert Röder et al.

It is certified that error appears in the above-identified patent and that said Letters Patent is hereby corrected as shown below:

Column 3, line 4, "chromtographic" should be -- chromatographic --.

Claim 6, line 2, "5" should be -- 1 --.

Claim 7, line 2, "7" should be -- 1 --.

Claim 8, line 1, "5" should be -- 7 --.

Signed and Sealed this

Eleventh Day of March 1986

[SEAL]

Attest:

Attesting Officer

DONALD J. QUIGG

Commissioner of Patents and Trademarks